(12) United States Patent
Elnajjar

(10) Patent No.: US 6,382,969 B1
(45) Date of Patent: May 7, 2002

(54) DENTAL ARTICULATOR

(76) Inventor: Jean J. Elnajjar, 6400 Westpark, Suite 265, Houston, TX (US) 77057

( * ) Notice: Subject to any disclaimer, the term of this patent is extended or adjusted under 35 U.S.C. 154(b) by 0 days.

(21) Appl. No.: 09/629,539

(22) Filed: Jul. 31, 2000

(51) Int. Cl.[7] ............................................. A61C 11/00
(52) U.S. Cl. ......................................................... 433/60
(58) Field of Search .............................. 433/54, 60, 64, 433/66, 213

(56) References Cited

U.S. PATENT DOCUMENTS

| | | | |
|---|---|---|---|
| 3,510,947 A | 5/1970 | Tuccillo et al. | |
| 4,319,875 A | 3/1982 | Beckwith | |
| 4,494,934 A | * 1/1985 | Huffman | 433/213 |
| 4,496,320 A | 1/1985 | Hwang | |
| 4,533,323 A | 8/1985 | Huffman | |
| 4,548,581 A | 10/1985 | Huffman | |
| 4,734,033 A | 3/1988 | Huffman | |
| 4,797,097 A | * 1/1989 | Cohn | 433/64 |
| 4,842,242 A | 6/1989 | Huffman | |
| 5,044,949 A | * 9/1991 | Xanthopoulos | 433/60 |
| 5,221,203 A | 6/1993 | Callne | |
| 5,360,337 A | * 11/1994 | Westdyk | 433/54 |
| 5,425,636 A | * 6/1995 | Ghim | 433/64 |
| 5,605,456 A | 2/1997 | Young | |
| 5,622,497 A | 4/1997 | Cho | |
| 5,645,425 A | * 7/1997 | Callne | 433/60 |
| 5,769,634 A | * 6/1998 | Choi | 433/64 |
| 5,996,963 A | * 12/1999 | Michael | 433/213 |

* cited by examiner

*Primary Examiner*—Todd E. Manahan
(74) *Attorney, Agent, or Firm*—Keeling Law Firm

(57) ABSTRACT

A dental articulator system including a device and method of forming dental casts with a posterior clip. The clip has a line of holes that receive male bulbs from a dental articulator. The dental articulator has adjustable ball and socket joints, which are secured in place with a hand tightenable screw. The device does not require any glue; thus the dental articulator is easily adjusted and reusable.

6 Claims, 4 Drawing Sheets

DENTAL ARTICULATOR

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of Invention

This invention relates to a device and method for a dental articulator for use with dental model casts. Specifically, the invention describes a dental articulator that is easily adjustable by the dental laboratory technician and/or dentist to align as desired the upper and lower dental model casts.

2. Related Art

Dental articulators, which hold and align together positive dental impressions, are well known in the prior art. Articulators are used to align the upper (maxilla) dental model with the lower (mandible) dental model, to simulate current or desired occlusion. By recreating the teeth and their occlusion (alignment) in model form, false teeth, caps and other dental prosthetics can be made in the precise size and shape necessary for the patient's mouth.

To create the dental models (casts), the dentist makes a negative impression of the patient's teeth. This impression may be a full mold (bilateral) or a partial quadrant mold (unilateral). The impression is obtained by filling a tray with thermoplastic material, and holding it against the patient's teeth and gums. After the thermoplastic material partially hardens (sets up), the tray is removed, leaving the negative impression of the teeth.

To form a positive impression of the teeth and their position, pourable hardenable stone, often called yellow stone, is poured into the negative impression. The positive impression is allowed to harden, and is then removed from the negative impression, forming a precise positive model of the teeth and their placement. The hard positive impression is then pressed into a forming mold containing new yellow stone. This yellow stone is in a flowable state and forms the base of the dental cast. The positive impression bonds with the new yellow stone base, excess yellow stone is scraped away, remaining yellow stone is allowed to harden, and the complete cast is now formed. This cast is then removed from the forming mold.

The casts (upper and lower) are then attached to a dental articulator, which emulates the patient's jaw for aligning the upper and lower teeth/casts.

The prior art describes various devices and methods for fashioning and securing the dental cast base to the positive impression. Prior art also describes various devices and methods for securing the dental casts to a dental articulator.

Representative of the early prior art for dental cast bases are devices described in the Tuccillo et al. U.S. Pat. No. 3,510,947 (May 12, 1970) and the Beckwith U.S. Pat. No. 4,319,875 (March 16, 1982). These patents utilize bases having female plastic snap receivers. The positive impressions are fabricated with male studs, which snap into the female snap receivers of the base. This requires precise alignment of each male stud to properly mate with the female receiver. Repeated use wears down the male stud, causing loose snapping with the female receiver, thus making the alignment loose.

An alternative base system is described in the Cho U.S. Pat. No. 5,622,497 (Apr. 22, 1997). A plastic base is adhered to a positive impression with a layer of stone material. The plastic base has a slot in which a disk is inserted and secured with a setscrew. The disk is attached to a stem having a ball at the other end, which connects to a reusable articulator. The system is requires plastic bases that are relatively expensive, as is the non-disposable dental articulator.

The most common type of base system, however, is the type utilized in the Huffman series of U.S. Pat. Nos. (4,533, 323; 4,548,581; 4,734,033; 4,842,242). These patents and several others utilize base formers. Soft stone material is placed into a (typically) rubber base former, having a continuous sidewall, a floor and an open top. A hard positive impression is pressed into the soft stone material, excess overflow material is scraped away, and the soft stone material allowed to harden, adhering to the positive impression. The base and positive impression combine to form the dental cast, which has a uniform appearance due to the similar stone used in both the base and positive impression.

Dental casts formed by pressing positive impressions into base formers are affixed to dental articulators in a variety of methods in the prior art. Young (U.S. Pat. No. 5,605,456—Feb. 25, 1997) utilizes a cam clamp of the type used to secure automotive hoses. This hose clamp is wrapped around the base of the dental cast, and secured to a substantial dental articulator. Callne (U.S. Pat. No. 5,221,203—Jun. 22, 1993) utilizes a wire loop that clips into brackets integral with the top of the base. The wire loop is attached to a screw wheel adjustable dental articulator. Both systems require articulators that are difficult to use and are expensive.

The Huffman patents utilize a variety of means to secure the dental base/cast to an articulator. Huffman utilizes a disposable single-use plastic articulator having hinged articulator arms with socket balls that snap into retention sockets mounted to the dental cast base. The retention sockets may be inserted into the still soft stone (Huffman '323), which requires the "proficiency and expertise of the technician" to decide when to insert the mounting such that a proper alignment and securement is achieved. Other Huffman methods involve slots formed in the base by a shelf protruding into the interior cavity of the base former. When the former is removed (peeled off), slots and/or channels remain, into which a ridge tab is inserted and glued. The ridge tab has a socket that accepts a socket ball of the single-use articulator. When the upper and lower casts are aligned, a drop of quick drying glue is placed on the socket ball, and held until set. Some of the limitations of the Huffman devices are 1) the difficulty in positioning the upper and lower casts while gluing their socket joints; 2) inability to make adjustments after gluing the socket joints; 3) inability to make adjustments/corrections to the lateral and vertical placement of the ridge tabs after gluing; 4) difficulty in storing dental casts due to space taken by the non-removable articulator; and 5) expense associated with not being able to reuse articulators on different casts.

It would therefore be useful improvement of the prior art for a dental articulator system to utilize existing techniques for forming positive impressions, mounting these positive impressions on bases that use common stone material, and is flexible in adjustability during and after attachment to a re-usable articulator.

BRIEF SUMMARY OF THE INVENTION

Accordingly, the objectives of this invention are to provide, inter alia, a new and improved dental articulator that:

is easily adjustable;

is inexpensive;

does not require the use of glue; and can interchange and re-use articulator arms between different sets of casts.

These objectives are addressed by the structure and use of the inventive device and method. Re-usable articulator arms attach via ball and socket joints to a base clip, which is adhered to the dental cast base during the base formation process. Gross horizontal alignment is accomplished by a plurality of female recesses that accommodate male bulbs of a clip that attaches to the articulator arm via a screw adjustable ball and socket joint. Vertical adjustment and fine horizontal adjustment are accomplished by adjusting the orientation of the articulator arm ball and socket joint.

Other objects of the invention will become apparent from time to time throughout the specification hereinafter disclosed.

DETAILED DESCRIPTION OF THE INVENTION

Figure 1:
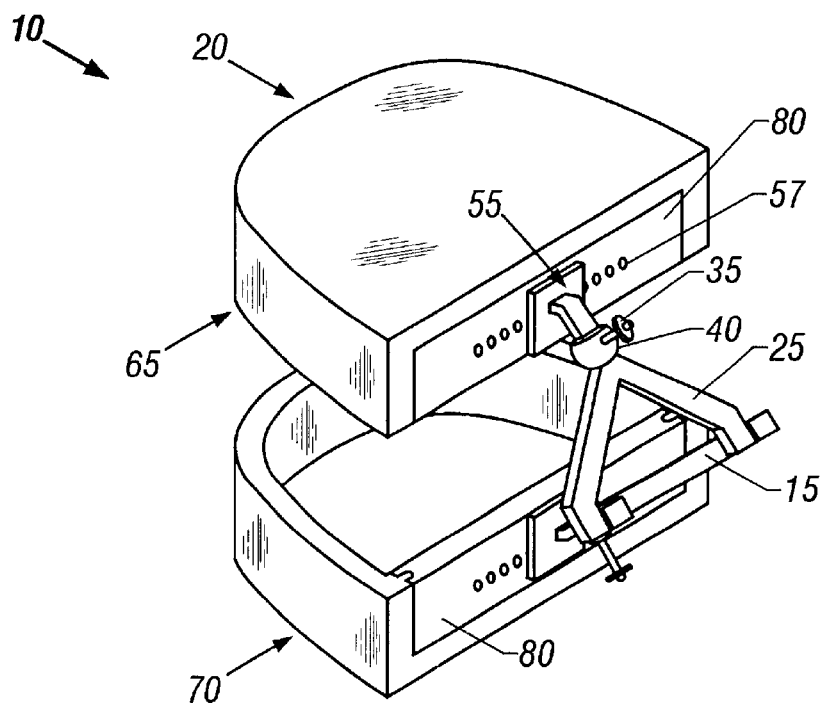
FIG. 1 depicts the inventive full arch former with articulator.
Figure 2:
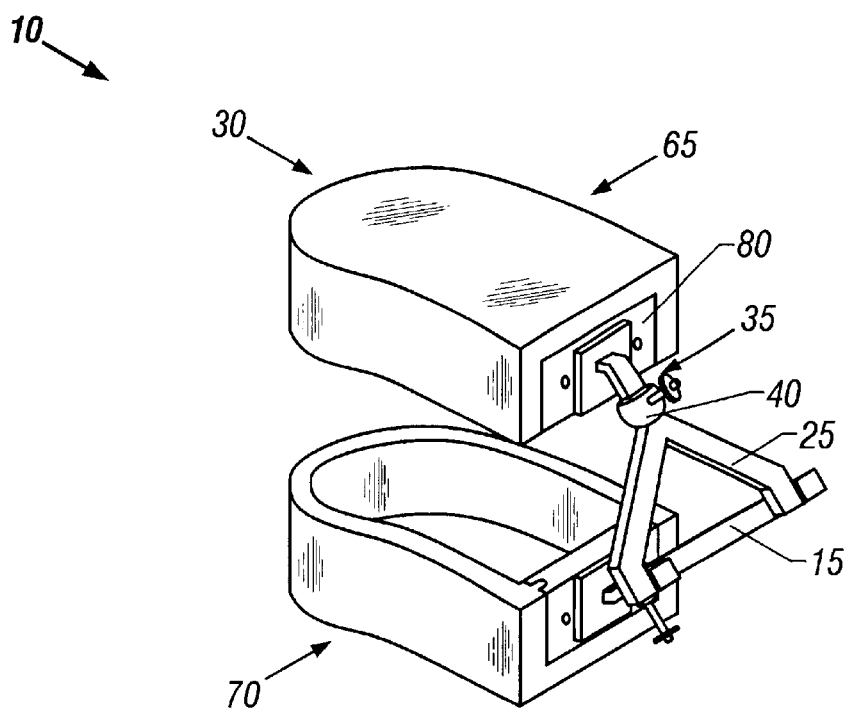
FIG. 2 depicts the inventive half arch (quadrant) former with articulator.

The present invention is described as dental articulator system 10, as depicted in FIGS. 1–7. Dental articulator system 10 comprises base former 60, sliding clip 80 and dental articulator 15. As seen in FIGS. 1 and 2, dental articulator system 10 can be a full arch articulator 20 or a half arch articulator 30.

Figure 3:
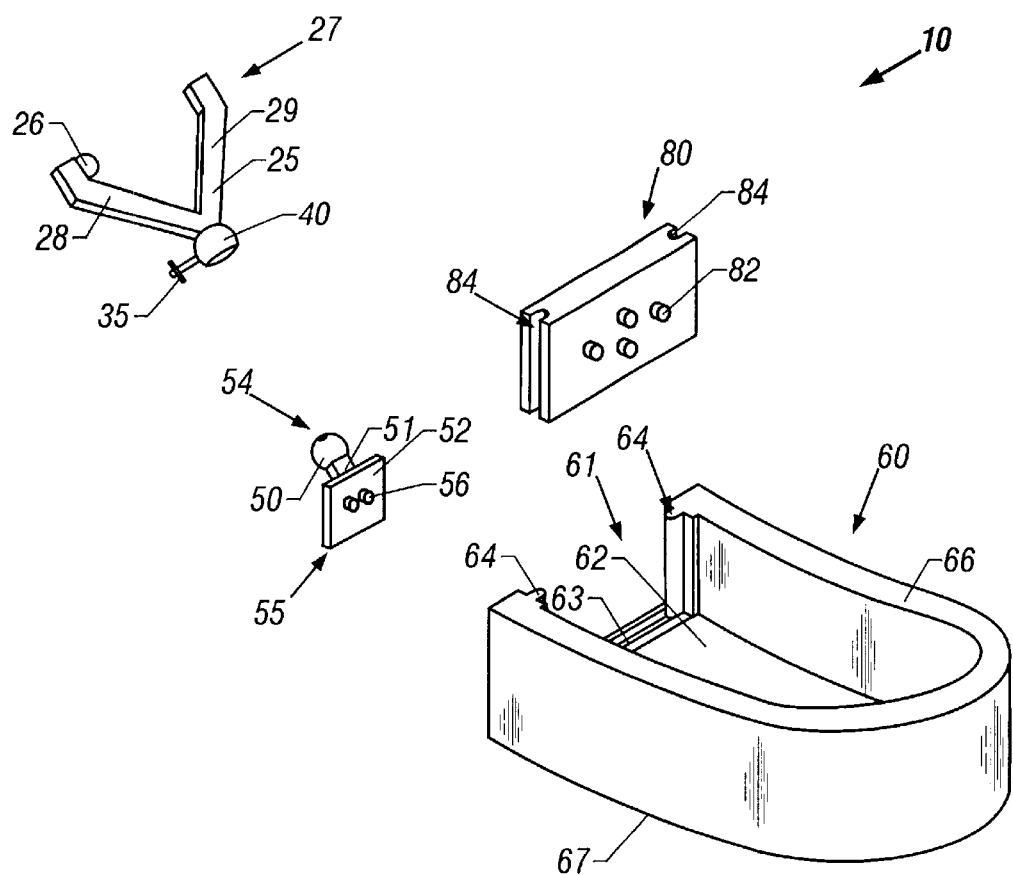
FIG. 3 depicts the inventive former and articulator in exploded view.
Figure 4:
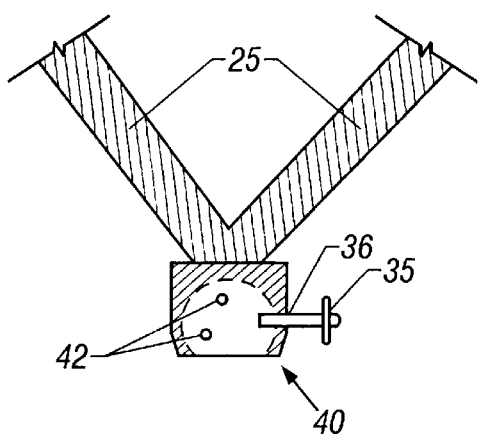
FIG. 4 depicts detail of the articulator arm adjustable ball and socket joint.

Base former 60, as seen in FIG. 3, is similar, if not identical, for the upper (maxilla) dental casting model and the lower (mandible) dental model. Upper maxillary base former 65 is used to form upper dental cast 76, and lower mandibular base former 70 is used to form lower dental cast 78. Base former 60 is preferably made of flexible rubber as known in the art for base formers. Base former 60 comprises a flexible former wall 67, said former wall 67 having a height adequate to hold casting stone upon which a positive impression can be pressed/bonded, and a thickness adequate to support lateral pressures of said casting stone. Base former further comprises former floor 62 to contain the casting stone.

Novel and unique to base former 60 is base former posterior opening 61, which is defined by two vertical ridge guides 64 protruding from the interior of former wall 67, and floor ridge 63, protruding normal from former floor 62. Sliding clip 80, as seen in FIGS. 1, 2 and 3, has a generally rectangular shape with clip channels 84 inset the length of each end. On one side of sliding clip 80 is a means of anchorage of sliding clip 80 to pourable hardenable casting stone. This means of anchorage is provided by a plurality of anchorage bulbs 82, typically protruding out ⅛" to ¼" inch, and having a diameter thickness of ⅛" to ¼". On the opposite side of sliding clip 80 are a plurality of sliding clip female recesses 57. Sliding clip female recesses 57 are horizontally aligned along the width of sliding clip 80, and provide different connection points for dental articulator 15. In the preferred embodiment, sliding clip 80 is made of hard plastic or similar material having rigid strength, capable of bonding to pourable hardenable casting stone, and able to accommodate and secure sliding clip male bulbs 56.

Sliding clip 80 slides into and occludes former posterior opening 61 by aligning clip channels 84 above ridge guides 64, and slidably connecting sliding clip 80 to former sides 67 by sliding ridge guides 64 through clip channels 84 until the base of sliding clip 80 seals against floor ridge 63. In one embodiment, a channel (not shown) traverses the bottom edge of sliding clip 80 to facilitate mating with floor ridge 63. In another embodiment, floor ridge 63 is missing, and the bottom of sliding clip 80 mates directly against the posterior portion of former floor 62 below former posterior opening 61.

Sliding clip 80 is connectable to attachment clip 55. Attachment clip 55 comprises clip plate 52, which comprises at least one, preferably a plurality in linear alignment, sliding clip male bulb 56. Sliding clip male bulb(s) 56 are capable of snapping into sliding clip female recess(es) 57 (FIG. 1). On the opposite side of clip plate 52 is attachment shaft 51, which connects to clip socket ball 50. All components of attachment clip 55 are preferably constructed of hard plastic or other material having adequate support strength and flexibility of engagement units, including sliding clip male bulb 56.

Clip socket ball 50 mates inside arm socket 40, which is connected to the v-base of articulator arm 25. Clip socket ball 50 is preferably a semi-split ball, allowing for partial compression while being inserted into arm socket 40, and then snapping back outwardly after insertion for a snug fit. Of course, alternatively clip socket ball 50 and arm socket 40 can switch places, such that attachment shaft 51 terminates in a socket and articulator arm 25 terminates to a ball, thus forming an equivalent ball-and-socket joint as described in detail herein. In the preferred embodiment, inside arm socket 40 (FIG. 4) is at least one resistance nib 42. Resistance nib 42 is a short nib protruding into the interior cavity of arm socket 40, and is sized to mate against one of the ball dimples 54 located on the exterior surface of clip socket ball 50. Arm socket 40 further comprises ball securement 35, which is a screw, preferably hand-tightenable, that projects into the interior of arm socket 40 through socket threaded channel 36. In the preferred embodiment, socket threaded channel 36 is threaded, but alternatively may be sized such that friction, adhesives, or similar securement means retain ball securement 35. Further, if threaded, socket threaded channel 36 should be capable of supporting axial and lateral forces exerted by ball securement 35 when ball securement 35 is screwed down tight. Thus, arm socket 40 should be composed of material strong enough to provide such support, such as metal or a hard plastic. Alternatively, socket threaded channel 36 may be lined with a threaded channel insert (not shown), typically metal, providing engagement support for ball securement 35.

After clip socket ball 50 is snapped into arm socket 40, it is locked into position by tightening down ball securement 35, which mates against a ball dimple 54 on clip socket ball 50. This force also engages at least one resistance nib 42 against another ball dimple 54, locking clip socket ball 50 in place. In the preferred embodiment, there are three resistance nibs 42 on the interior surface of arm socket 40 placed 120° apart as measured on arcs of the sphere defined by the interior of arm socket 40, with ball securement 35 also positioned 120° from the three resistance nibs 42. Alternatively, there are two resistance nibs 42 placed 120° apart on a plane with ball securement 35, such that the two resistance nibs 42 and ball securement 35 are each 120° apart. Alternatively, only one resistance nib 42 is interior arm socket 40, and is oriented opposite ball securement 35. The selected orientation of resistance nibs 42 relative to ball securement 35 afford uniform force against clip socket ball 50, thus providing maximum locking support.

Figure 5A:
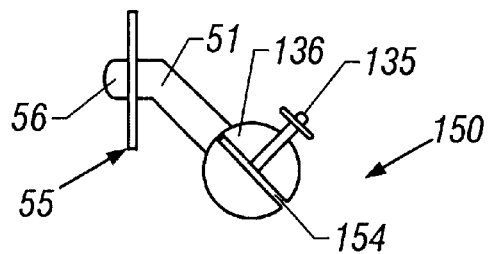
FIGS. 5a and 5b depict an alternative preferred embodiment of the articulator arm adjustable ball and socket joint.
Figure 5B:
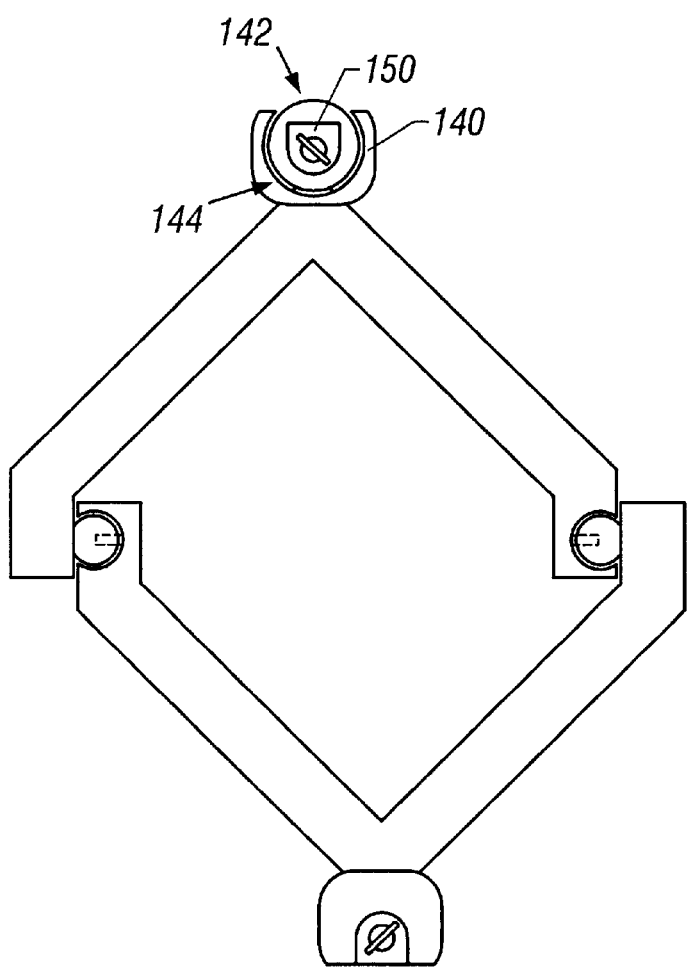

In an alternative embodiment, arm socket 40 is replaced by a arm open socket 140, and clip socket ball 50 is replaced by clip socket expandable ball 150, as shown in FIGS. 5a and 5b. Arm open socket 140 comprises ball opening 142, through which clip socket expandable ball 150 is inserted, and expander opening 144, which affords access and movement for ball expander 135. Ball opening 142 and expander opening 144 are sized small enough such that clip socket expandable ball 150 is supported and retained when expanded. Ball opening 142 is sized large enough to afford insertion of expandable socket ball 150. Expander opening 144 is sized large enough to allow lateral rotation of expandable socket ball 150 during alignment prior to tightening of expandable socket ball 150. Preferably, within the interior of arm open socket 140 are resistance nibs 42, which impede against ball dimples 54 as in the first preferred embodiment. Ball expander 135 screws through ball threaded channel 136 through a first half of the split clip socket expandable ball 150. Ball expander 135 terminates against a second half of the split clip socket expandable ball 150 against ball interior split surface 154, pushing against it and spreading apart expandable socket ball 150.

Dental articulator 15, as seen in FIGS. 1 and 2, comprises two articulator arms 25. Each articulator arm 25 comprises a ball arm 28 and a socket arm 29 that meet at arm socket 40. Ball arm 28 and socket arm 29 emerge diversely away from arm socket 40. At the end opposite arm socket 40, ball arm 28 comprises an articulator arm socket ball 26. At the end opposite from arm socket 40, socket arm 29 comprises an articulator arm socket 27. Two articulator arms 25 mate together to form a movable hinge. This mating is accomplished by articulator arm socket ball 26 from a first articulator arm 25 snapping into an articulator arm socket 27 of a second articulator arm 25, while simultaneously articulator arm socket ball 26 from a second articulator arm 25 snaps into an articulator arm socket 27 of the first articulator arm 25, as seen in FIG. 1 and 2. Articulator arm socket balls 26 are preferably semi-split, allowing them to compress while snapping into articulator arm socket 27, and then releasing outwardly to provide a snug fit to provide friction resistance for smooth hinge action.

OPERATION

Figure 6:
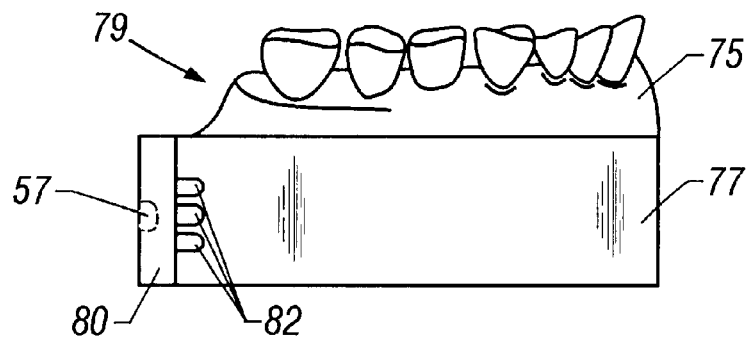
FIG. 6 depicts a dental cast with the inventive attachment sliding clip.

Former posterior opening 61 is first occluded by sliding along ridge guides 64 sliding clip 80, forming base former 60 as a receptacle. Optionally, a lubricant can be sprayed or wiped on the interior surface of former floor 62 and/or former wall 67, but not sliding clip 80, to afford ease in later peeling away base former 60 from the hardened casting stone. Pourable hardenable casting stone is poured into base former 60, flowing around anchorage bulbs 82. The positive dental impression 75 is then pressed into the soft stone, and excess soft stone flowing over former top edge 66 is wiped or scraped away. The positive dental impression 75 is positioned in base former 60 such that is protrudes away from the soft stone to emulate the patient's dental orientation, as is typical in the art. As the soft stone hardens forming base 77, it binds to the positive dental impression, which together form dental cast 79 (FIG. 6).

When dental cast 79 has hardened, base former 77 is pulled away for later re-use, leaving dental cast 79 with sliding clip 80 embedded and attached via the surface of sliding clip 80 and anchorage bulbs 82. As seen in FIGS. 1 and 2, sliding clip 80 comprises a plurality of sliding clip female recesses 57 that are horizontally aligned.

In the preferred embodiment, dental articulator 15 is pre-assembled. Two articulator arms 25 are snapped together by snapping articulator arm socket balls 26 into articulator arm sockets 27, forming a hinged connection. Clip socket balls 50 are snapped into each arm sockets 40, and ball securement 35 is left untightened.

Figure 7:
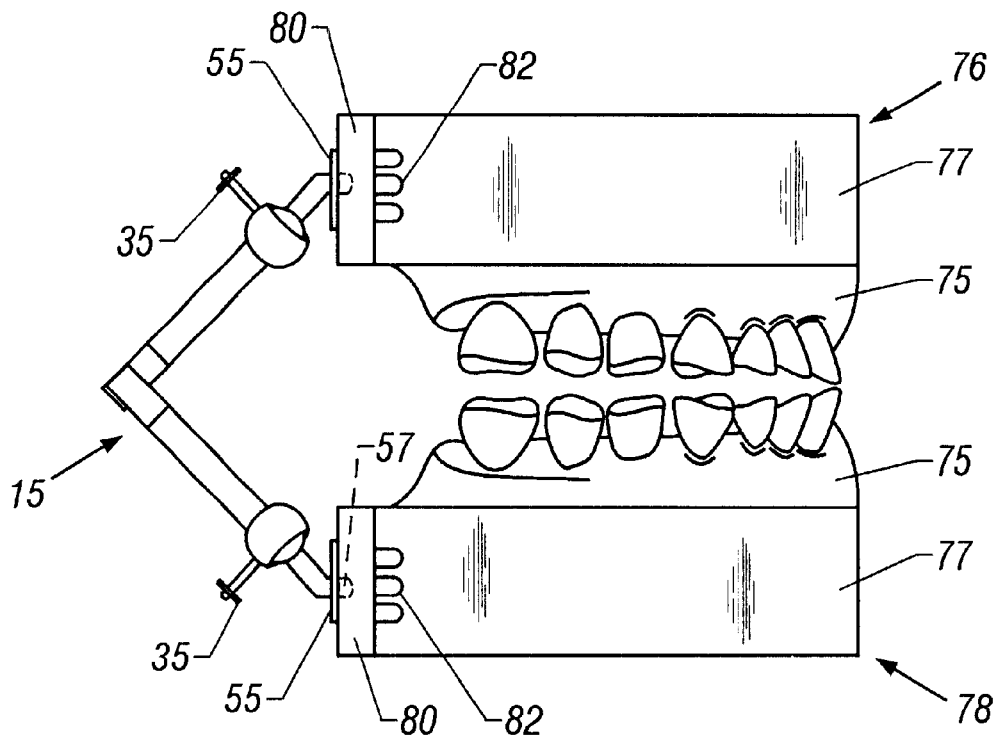
FIG. 7 depicts the inventive articulator attached to upper and lower dental casts.

Upper dental cast 76 and lower dental cast 78 are aligned to mechanically simulate axes of articulation, planes and arcs of occlusion, lines, planes and axes of symmetry found in the patient's mouth, as seen in FIG. 7. Attachment clips 55, each having preferably at least two sliding clip male bulbs 56 horizontally aligned and spaced equal to the spacing of sliding clip female recesses 57, snap into the upper and lower sliding clips 80 such that upper dental cast 76 and lower dental cast 78 are roughly aligned horizontally, and the upper attachment clip 55 is roughly aligned vertically with the lower attachment clip 55, preferably in the centers of sliding clips 80.

Fine vertical and horizontal alignment adjustments of the upper and lower dental casts are made while the ball securements 35 are still loose. When the alignment of the upper and lower dental casts is proper, the ball securements 35 are tightened down, impinging on ball dimples 54 and pressing clip socket ball 50 against resistance nibs 42 inside arm socket 40. In the alternative preferred embodiment utilizing clip socket expandable ball 150, ball expander 135 is screwed down, pressing against ball interior split surface 154. As additional pressure is placed against ball interior split surface 154, clip socket expandable ball 150 expands, impinging against resistance nibs 42 inside arm open socket 140. At this stage, the only dental articulator 15 free movement is that which is about the hinge formed by articulator arm socket ball 26 and articulator arm socket 27. Thus, the upper dental cast 76 and lower dental cast 78 are free to rotate vertically in simulation of the patient's natural jaw motion.

By unsnapping attachment clips 55 of articulator arm 15 off sliding clips 80 of the dental casts, the dental casts can be shipped and stored in a smaller volume, thus providing additional storage space and smaller shipping containers. Articulator arm 15 can easily be snapped in and adjusted by the dentist, the dental technician or the laboratory technician. The same articulator arm 15 can be re-used on any dental cast 79 having the inventive sliding clip 80.

The foregoing disclosure and description of the invention is illustrative and explanatory thereof. Various changes in the details of the illustrated construction may be made within the scope of the appended claims without departing from the spirit of the invention. The present invention should only be limited by the following claims and their legal equivalents.

I claim:

1. A dental articulator system comprising:
   at least one flexible base former;

each base former comprising a flexible former wall, an opening in said flexible former wall, a former floor and a sliding clip;

said sliding clip capable of occluding said opening in said flexible former wall;

said sliding clip comprising a means of anchorage to a pourable hardenable casting stone;

said sliding clip removable from the remainder of said flexible base former;

at least one attachment clip and at least one articulator arm;

each said attachment clip having a slide clip end and an arm end;

each said attachment clip slide clip end connectable to a corresponding said sliding clip;

a ball and socket joint connecting each said attachment clip arm end and each said articulator arm;

each said ball and socket joint comprising a socket and a socket ball;

each said socket ball oriented within a corresponding said socket;

a screw traversing through said socket and onto said ball; and said screw operable to impinge against said socket ball against an inner wall of said socket.

2. The dental articulator system as in claim 1, further comprising:

said at least one articulator arm comprising a first articulator arm and a second articulator arm; and at least one articulator arm ball and socket joint connecting said first articulator arm and said second articulator arm.

3. The dental articulator system as in claim 1, wherein:

said sliding clips each further comprising a plurality of sliding clip female recesses;

each said sliding clip female recess opening away from said base former within an outer surface of said sliding clip; and each said attachment clip side end comprising a plurality of sliding clip male bulbs, each said sliding clip male bulb snapping into one said sliding clip female recess.

4. The dental articulator system as in claim 1, further comprising:

each said socket ball comprising a plurality of dimple indentations on a surface of each said socket balls;

each said sockets comprising at least one resistance nib protruding away from an inner surface of said socket; and each said screw traversing through each said socket, and each said resistance nib interfacing with said plurality of dimple indentations to increase impingement capability of each said ball securement means.

5. A dental articulator system comprising:

at least one flexible base former;

each base former comprising a flexible former wall, an opening in said flexible former wall, a former floor and a sliding clip;

said sliding clip capable of occluding said opening in said flexible former wall;

said sliding clip comprising a means of anchorage to a pourable hardenable casting stone, said sliding clip removable from the remainder of said flexible base former;

a first attachment clip, a second attachment clip, a first articulator arm and a second articulator arm;

each said attachment clip having a slide clip end and an arm end;

each said attachment clip slide clip end connectable to a corresponding said sliding clip;

a first expandable ball and a first open socket joint connecting said first attachment clip arm end and said first articulator arm;

a second expandable ball and a second open socket joint connecting said second attachment clip arm end and said second articulator arm;

each said expandable ball and open socket joint comprising an arm open socket connected to each said articulator arm and a split expandable ball connected to each said attachment clip arm end;

each said split expandable ball oriented within said arm open socket;

a ball expander means comprising a screw traversing through a first half of said split expandable ball;

said ball expander means pressing against a ball interior split surface of a second half of said split expandable ball; wherein said split expandable ball impinging against an inner surface of said arm open socket as said ball expander means engages.

6. The dental articulator system as in claim 5, further comprising:

said split expandable ball comprising a plurality of dimple indentations on a surface of said split expandable ball; and said arm open socket comprising at least one resistance nib protruding away from said inner surface of said arm open socket.

* * * * *